United States Patent [19]

Puri

[11] Patent Number: 5,048,328

[45] Date of Patent: Sep. 17, 1991

[54] METHOD OF DETERMINING THE POROSITY AND IRREDUCIBLE WATER SATURATION OF A COAL CLEAT SYSTEM

[75] Inventor: Rajen Puri, Tulsa, Okla.

[73] Assignee: Amoco Corporation, Chicago, Ill.

[21] Appl. No.: 315,007

[22] Filed: Feb. 24, 1989

[51] Int. Cl.$^5$ ............................................. E21B 47/00
[52] U.S. Cl. ................................................... 73/153
[58] Field of Search ........................... 73/152, 153, 38

[56] References Cited

U.S. PATENT DOCUMENTS

| | | | |
|---|---|---|---|
| 4,245,313 | 1/1981 | Coates | 73/152 |
| 4,413,512 | 11/1983 | Zemanek, Jr. | 73/152 |
| 4,506,548 | 3/1985 | Zemanek, Jr. | 73/152 |
| 4,756,189 | 7/1988 | Fertl et al. | 73/152 |

*Primary Examiner*—Hezron E. Williams
*Assistant Examiner*—Craig Miller
*Attorney, Agent, or Firm*—Fred E. Hook; L. Wayne White

[57] ABSTRACT

The irreducible water saturation profile across the length of a core sample of coal is determined from four series of X-ray attenuation measurements made over the length of the core sample. The X-ray attenuation measurements are made while the core sample is at a pressure simulating a formation overburden pressure. The first series of X-ray attenuation measurements are made while the core sample is saturated with distilled water or formation brine. The distilled water or formation brine is then displaced with humidified, inert, substantially nonadsorbing gas and a second series of X-ray attenuation measurements are made. The core sample is then saturated with an aqueous sodium iodide solution and a third series of X-ray attenuation measurements are made. The aqueous sodium iodide solution is then displaced with a humidified, inert, substantially nonadsorbing gas and a fourth series of X-ray attenuation measurements are made.

4 Claims, 2 Drawing Sheets

METHOD OF DETERMINING THE POROSITY AND IRREDUCIBLE WATER SATURATION OF A COAL CLEAT SYSTEM

BACKGROUND OF THE INVENTION

1. Field of the Invention

This invention pertains to a method of determining the porosity and the irreducible water saturation associated with a coal cleat network. These parameters are useful in determining the amount of mobile water in a coal seam. Mobile water is water-in-place in the coal seam which will have to be removed and disposed of during coal degasification operations.

2. Description of the Prior Art

Coal is the most abundant fossil fuel in the world. Its recoverable reserves amount to almost 100 quintillion BTU of energy, nearly 15 times the total energy content estimated for known reserves of petroleum. *Petroleum Frontiers*, vol. 3, no. 4, pages 2-3 (1986), published by Petroleum Information Corporation. People have mined coal and used it for heat for centuries. However, it is within the recent past that coal has been recognized for being the origin and source for coalbed methane, another valuable hydrocarbon fuel. "Coalbed methane" consists primarily of methane (e.g., 95%) but may also contain ethane, propane, and higher homologs. The volume of coalbed methane is estimated to be about 400 trillion standard cubic feet (SCF) of gas in place, most of it adsorbed on coal in seams buried at a depth of less than 9000 feet (ft) from the surface, and almost half of it is on coal seams buried less than 3000 ft, too deep to mine but easily penetrated by a wellbore using conventional drilling techniques. Coalbeds are, therefore, reservoirs and source rocks for a huge amount of gas which can be produced, in part, through a wellbore. Methods of recovering the gas (i.e., coal degasification methods) are shown, for example, by U.S. Pat. No. 4,471,840, U.S. Pat. No. 4,391,327 and U.S. Pat. No. 4,301,875.

Much work has been done to capture the prize. The U.S. Department of Energy and the Gas Research Institute have funded a substantial amount of research on coal degasification and the results have been published in the open literature. In addition, periodic coalbed methane symposiums are held at the University of Alabama, and elsewhere, and the results published as symposium proceedings. Many of the journal articles highlight the significance of determining the water-in-place in the coal seam which will have to be removed and disposed of during coal degasification operations. The present invention is directed to this technical problem.

Coal is a dual porosity rock consisting of micropores (matrix) and a network of natural fractures known as cleats. At discovery, the cleat network and matrix micropores in a coal seam are completely saturated with water and methane is adsorbed to the surface of coal. Reservoir pressure depletion is the only mechanism currently being employed to desorb methane from coal. When production of coalbed methane is initiated, water contained in the coal cleat network flows to the wellbore, as per Darcy's Law. This leads to a reduction in reservoir pressure which in turn desorbs methane from the coal surface. Gas production rate from a well is accordingly directly influenced by the speed with which a coal seam is de-watered. While methane migrates from the coal matrix to the cleat network by diffusion, the water contained in the coal micropores (typically 40 Angstrom or smaller pores linked by 5 Angstrom passages) remains essentially immobile due to strong capillary forces. Thus, even though most of the porosity in coal is contained within the micropores, only the cleat porosity and its irreducible water saturation are of importance to a coalbed methane project.

The present invention provides a means for determining the porosity and irreducible water saturation associated with a coal cleat network.

SUMMARY OF THE INVENTION

A novel method of determining the irreducible water saturation, $S_{wr}$, profile across the length of a core sample of coal has been discovered, and from this information, the cleat porosity of the coal cleat network can be determined. As used herein, the water saturation in the coal cleat network is defined to be "irreducible" when humidified gas flow through a core sample is unable to displace any additional water during the laboratory test.

The method of determining $S_{wr}$ is a nondestructive method which comprises the steps of:

Step 1:
(a) applying pressure simulating a formation overburden pressure on a core sample of coal in a hydrostatic core holder;
(b) flowing distilled water or formation brine into and through the pressurized core holder until the sample is saturated with water;
(c) scanning the sample over its length with a linear X-ray device or CAT-scan to obtain a measure of the magnitude of X-ray attenuation of the sample, the values of X-ray intensity being denoted as $I^1$;

Step 2:
(a) flowing a humidified, inert, substantially nonadsorbing gas into and through the core holder until no additional water is displaced from the coal sample by the flowing gas;
(b) scanning the sample over its length with the X-ray device to obtain a measure of the magnitude of X-ray attenuation of the sample, the values of X-ray intensity being denoted as $I^2$;

Step 3:
(a) flowing X-water into and through the pressurized core holder until the sample is saturated with X-water;
(b) scanning the sample over its length with the X-ray device to determine a measure of the magnitude of X-ray attenuation of the sample, the values of X-ray intensity being denoted as $I^3$;

Step 4:
(a) flowing a humidified, inert, substantially nonabsorbing gas into and through the pressurized core holder until no additional X-water is displaced from the coal sample by the flowing gas;
(b) scanning the sample over its length with the X-ray device to determine a measure of the magnitude of X-ray attenuation of the sample, the values of X-ray intensity being denoted as $I^4$;

Step 5:
(a) determining the irreducible water saturation, $S_{wr}$, profile in the coal cleat network across the length of the core sample of coal using the following equation:

$$S_{wr} = \frac{\ln (I^2/I^4)}{\ln (I^1/I^3)},$$

wherein $S_{wr}$, $I^1$, $I^2$, $I^3$, and $I^4$ have the meanings set forth above;

wherein said hydrostatic holder is equipped with injection means for injecting fluids at an upstream end and with discharge means for removing displaced fluid through a downstream end of said holder; and wherein the X-ray device measures the X-ray attenuation over the same or essentially the same portion of the sample in each of Steps 1–4 above.

The total cleat porosity of the coal is then determined by a method comprising the steps of:

(a) measuring the volume of mobile water, $V_{mw}$, in a core sample of coal at a pressure, P, simulating a formation overburden pressure on the sample;

(b) measuring the bulk volume, $V_b$, of the sample;

(c) determining the arithmetic average irreducible water saturation, $S_{wr}$, of the sample at P; and (d) determining the total cleat porosity of the sample at P using the following equation:

$$\Phi_t = \Phi_e/(1 - S_{wr}),$$

wherein $\Phi_e = V_{mw}/V_b$ = effective cleat porosity of the sample.

These new analytical procedures provide an effective technique for obtaining the porosity and irreducible water saturation of the coal cleat network.

DETAILED DESCRIPTION OF THE INVENTION

Figure 1:
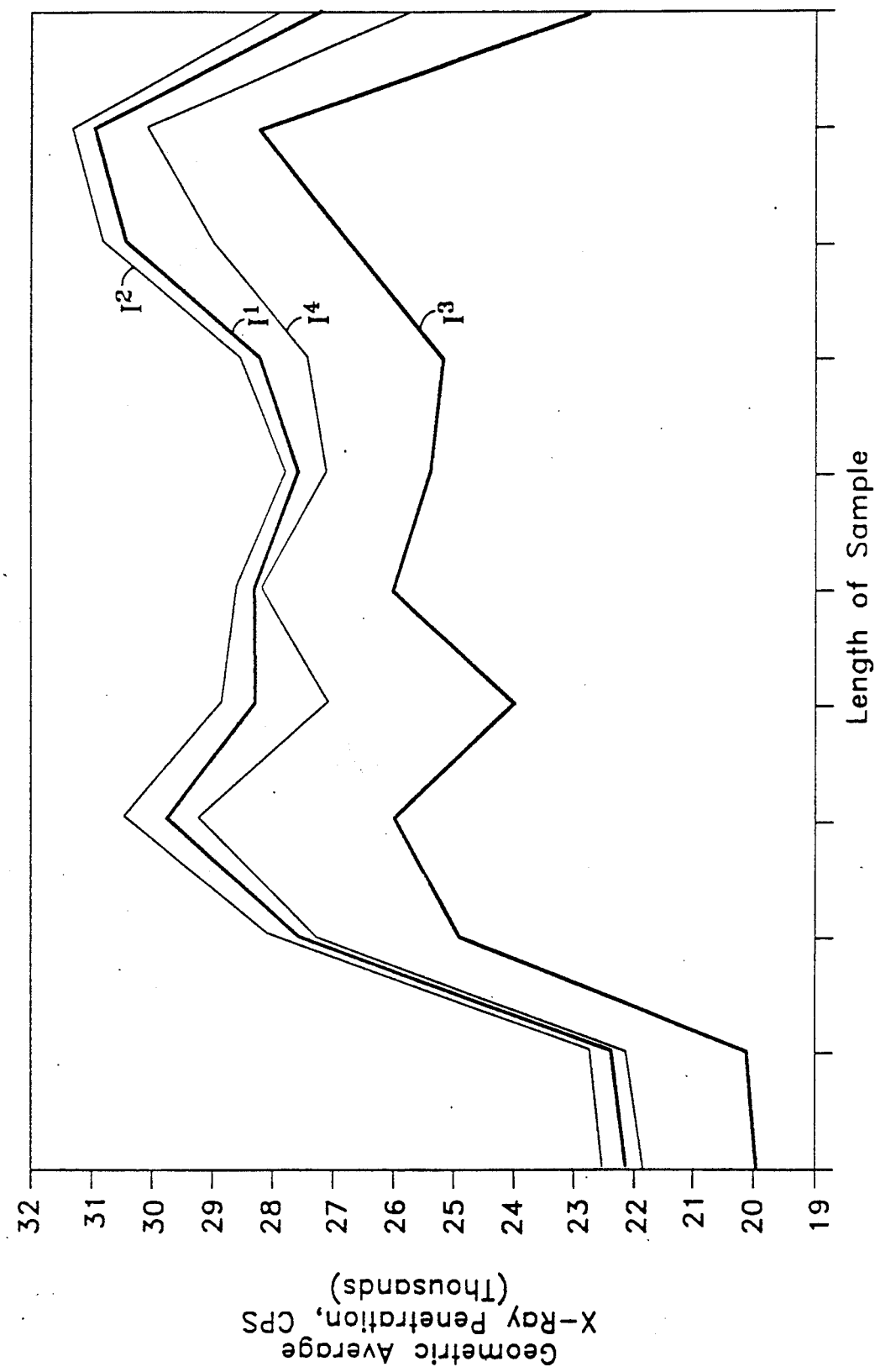
FIG. 1 shows a plot of X-ray intensities along the length of a coal core in accordance with Steps 1—4 of the test procedure.

The mechanical properties of coal are such that it tends to break easily. Damage to a portion of coal during the coring operation is common. Experience has shown that if adequate precautions are not taken to prevent the mishandling and weathering (drying and oxidation due to exposure to air and heat) of the remaining coal, artificial fractures are easily induced that render the core samples useless for any future laboratory testing. Special care is needed to maintain coal cores in their native state at all times. Furthermore, experience has also shown that whole diameter coal cores are best suited for making measurements of cleat porosity and irreducible water saturation in coal. Normally such whole diameter coal cores have a diameter of at least 2 inches, and cores having a diameter of about 3–4 inches or larger are not uncommon and are preferred.

SAMPLE SELECTION AND PREPARATION

The following procedure provides competent coal samples for conducting core tests in the laboratory:

(1) Cut whole diameter cores using an aluminum sleeve core barrel. As soon as the core barrel is retrieved from the well, section in 3 ft (or more) lengths and seal with rubber end caps. Make perforations in the rubber end caps to allow desorbing methane gas to escape. Carefully transport core sample cylinders to the testing facility.

(2) Place the aluminum core cylinder in a trough of water. Open the end caps and gently push out the coal core. Breakage of coal cores during this operation can be minimized if the aluminum core barrel and coal sample being retrieved are maintained in a horizontal position.

(3) After washing the core with water, select one or more coal samples from the core that visually appears to be high quality coal (i.e., low ash/shale content) and well cleated. Care should be taken in handling the samples to prevent breakage and to keep them water wet at all times.

(4) Dimensions, weight, bulk volume, and density measurements for each coal sample are then made and recorded. Small chips and cracks on the surface of the samples are filled with epoxy, the sample is wrapped in TEFLON tape, and a segment of plastic tubing is heat-shrunk over it. This helps prevent disaggregation during handling. The coal samples are then cut to a ri9ht cylinder and stored under water.

(5) Computer Aided Tomography (CAT-Scan) images of the right cylinder sections of core from (4) above are taken so that the cleat network may be examined over the length of each sample. Core samples that are found to be highly cleated and substantially free of shale barriers are then selected for testing according to the following procedure.

TEST PROCEDURE

Step 1: Place the selected section of coal core in a hydrostatic core-holder under the desired effective overburden pressure condition. Flow distilled water or formation brine into and through the pressurized core holder until 100% water saturation is established throughout the core (usually this takes 24 hours or less, and 24 hours is selected for convenience). Using an X-ray device, such as a CAT-Scan or linear X-ray device, measure the magnitude of X-ray attenuation at several locations over the entire length of sample. The X-ray intensities during this step will be denoted by Il Note that the exact orientation of the core-holder in the X-ray device should not be changed until all steps of this test procedure have been completed.

Step 2: Inject a humidified, inert, substantially nonadsorbing gas (such as nitrogen or helium) at the upstream face of the sample and measure the volume of produced water. This represents the "mobile water" in the cleat network. It is recommended that gas flow be continued for about 8 hours or more beyond the time when no measurable water is displaced from the coal sample. Scan the sample once again with the X-ray device at exactly the same locations as Step 1. The X-ray intensities during this step will be denoted by $I^2$.

Step 3: Prepare "X-water" by dissolving 150 grams (gms) of sodium iodide (NaI) per liter of distilled water. Flow X-water through the coal sample until the sample is fully saturated (a minimum of 24 hours is recommended). Scan the sample over its entire length and obtain a measure of the magnitude of X-ray attenuation at exactly the same locations as Steps 1 and 2. The X-ray intensities during this step will be denoted by $I^3$.

Step 4: Inject a humidified, inert, substantially nonadosrbing gas at the upstream face of the sample and measure the volume of produced water. This volume of water should match the volume obtained in Step 2 above. Once again, it is recommended that gas flow be continued for about 8 hours or more beyond the time when no measurable water is displaced from the coal sample. Note that the amount of water recovered from the core during Step 4 should equal that in Step 2. Scan the sample over its entire length and obtain a measure of the magnitude of X-ray attenuation at exactly the same locations as Steps 1, 2, and 3. The values of X-ray intensity during this step will be denoted in general by $I^4$.

FIG. 1 shows a plot of X-ray intensities during steps 1-4 on a coal sample. Geometric averaging of X-ray attenuation values over a small length (say 1 cm) is recommended.

CALCULATION OF IRREDUCIBLE WATER SATURATION IN COAL CORE

The irreducible water saturation at any location across the length of the core is obtained as follows:

$$S_{wr} = \frac{\ln(I^2/I^4)}{\ln(I^1/I^3)}$$

Figure 2:
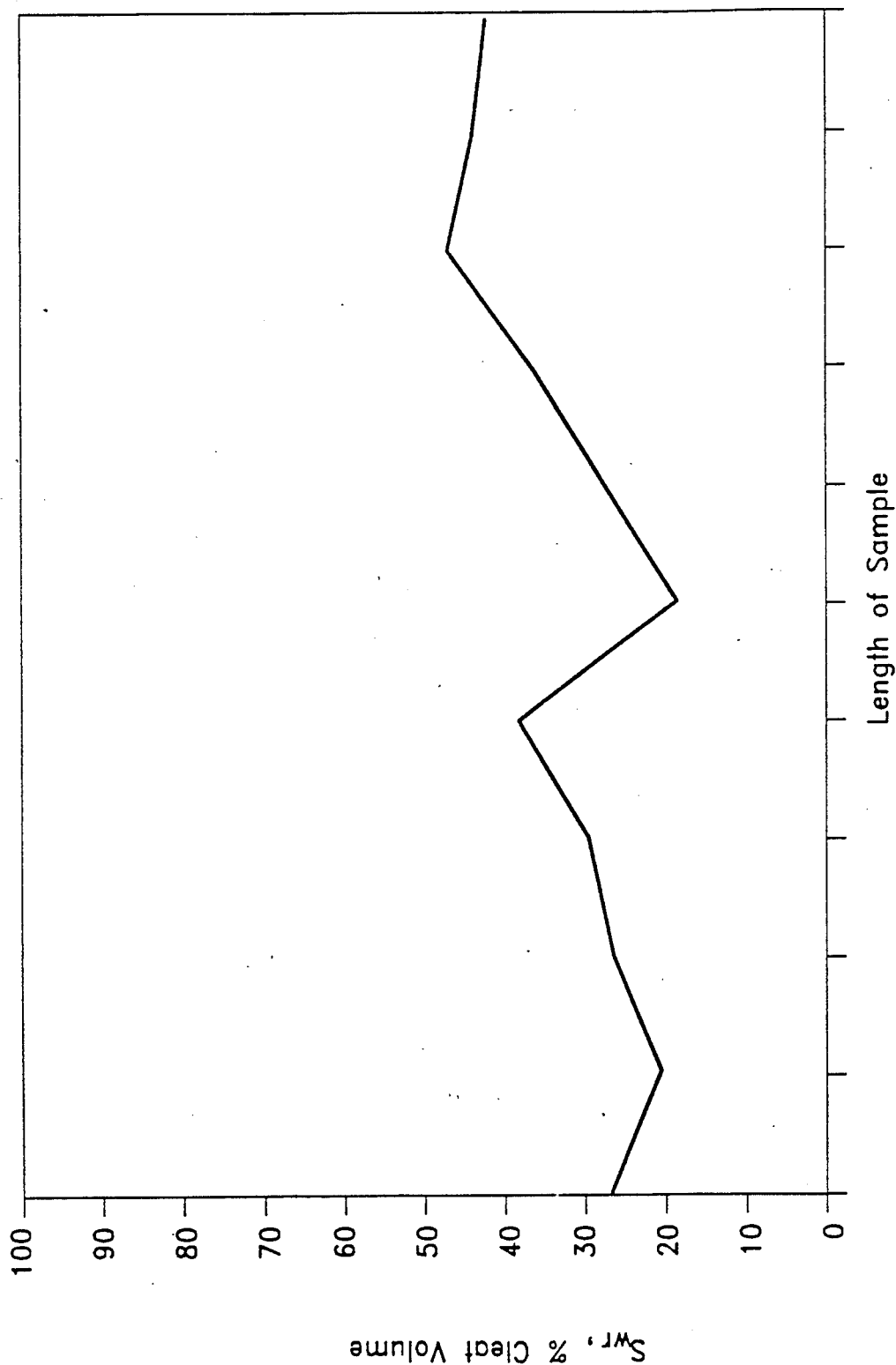
FIG. 2 shows a plot of irreducible water saturation values, $S_{wr}$, along the length of a coal core. The arithmetic average of $S_{wr}$ is derived from this plot.

FIG. 2 shows the irreducible water saturation profile in the coal cleat network calculated from FIG. 1.

The average irreducible water saturation in the cleat network of coal sample is determined by taking an arithmetic average of all the irreducible water saturation values. From FIG. 2, the average irreducible water saturation of the coal tested was 32.5%.

CALCULATION OF MOBILE WATER IN A COAL CORE

Mobile Water in a coal core is determined experimentally in Steps 2 and 4 in the Test Procedure. Mobile Water is represented by the term $V_{mw}$.

CALCULATION OF CLEAT POROSITY IN COAL CORE

The effective cleat porosity, $\Phi_e$, can be defined by the equation:

$$\Phi_e = (V_{mw})/V_b$$

where
$V_b$ = Bulk volume of the coal core and $V_{mw}$ = Volume of mobile water in the coal cleat network, value measured directly in Steps 2 and 4 above. In the above example, the $V_{mw}$ was 2.8 cc, the $V_b$ was 191.8 cc, and $\Phi_e$ was 1.46%.

The effective cleat porosity represents the maximum amount of water (as a fraction of the bulk volume of coal) that can be recovered from the coal cleat network. The total cleat porosity of coal is calculated as follows:

$$\Phi_t = \Phi_e/(1-S_{wr})$$

In the above example, $S_{wr}$ was 0.325; $\Phi_e$ was 1.46%; and $\Phi_t$ was 2.15%.

In coals with very low cleat porosity, the accuracy of cleat porosity and irreducible water saturation measurements can be improved if a low concentration X-Water (e.g., 75 gms of NaI per liter of solution) is substituted for distilled water or formation brine in Step 1.

CALCULATION OF MOBILE WATER IN A COAL SEAM

The method of determining the mobile water in a coal seam comprises the steps of (a) determining the irreducible water saturation, $S_{wr}$, and total cleat porosity, $\Phi_t$, of said coal using whole core samples, and (b) determining the amount of mobile water in a coal seam according to the equation $$\text{Mobile Water} = V_{coal}\Phi_t(1-S_{wr})$$

where
$V_{coal}$ is the volume of coal seam being drained for coalbed methane recovery.

What is claimed is:

1. A nondestructive method of determining the irreducible water saturation, $S_{wr}$, profile across the length of a core sample of coal, said method comprising the steps of:

Step 1:
(a) applying pressure simulating a formation overburden pressure on a core sample of coal in a hydrostatic core holder;
(b) flowing distilled water or formation brine into and through the pressurized core holder until the sample is saturated with water;
(c) scanning the sample over its length with a linear X-ray device or CAT-scan to obtain a measure of the magnitude of X-ray attenuation of the sample, the values of X-ray intensity being denoted as $I^1$;

Step 2:
(a) flowing a humidified, inert, substantially nonadsorbing gas into and through the core holder until no additional water is displaced from the coal sample by the flowing gas;
(b) scanning the sample over its length with the X-ray device to obtain a measure of the magnitude of X-ray attenuation of the sample, the values of X-ray intensity being denoted as $I^2$;

Step 3:
(a) flowing X-water into and through the pressurized core holder until the sample is saturated with X-water;
(b) scanning the sample over its length with the X-ray device to determine a measure of the magnitude of X-ray attenuation of the sample, the values of X-ray intensity being denoted as $I^3$;

Step 4:
(a) flowing a humidified, inert, substantially nonabsorbing gas into and through the pressurized core holder until no additional X-water is displaced from the coal sample by the flowing gas;
(b) scanning the sample over its length with the X-ray device to determine a measure of the magnitude of X-ray attenuation of the sample, the values of X-ray intensity being denoted as $I^4$; and Step 5:
(a) determining the irreducible water saturation, $S_{wr}$, profile in the coal cleat network across the length of the core sample of coal using the following equation:

$$S_{wr} = \frac{\ln(I^2/I^4)}{\ln(I^1/I^3)},$$

wherein $S_{wr}$, $I^1$, $I^2$, $I^3$, and $I^4$ have the meanings set forth above;
wherein said hydrostatic holder is equipped with injection means for injecting fluids at an upstream end and with discharge means for removing displaced fluid through a downstream end of said holder; and wherein the X-ray device measures the X-ray attenuation over the same or essentially the same portion of the sample in each of Steps 1–4 above.

2. The method defined by claim 1 wherein said gas is nitrogen or helium.

3. The method defined by claim 2 wherein said X-ray device is a linear X-ray device.

4. The method defined by claim 2 wherein said X-ray device is a CAT-scan device.

* * * * *